United States Patent [19]

Marko

[11] Patent Number: 5,493,043
[45] Date of Patent: Feb. 20, 1996

[54] METHOD FOR REDISTRIBUTION AND PURIFICATION OF METHYLSILANES

[75] Inventor: Ollie W. Marko, Carrollton, Ky.

[73] Assignee: Dow Corning Corporation, Midland, Mich.

[21] Appl. No.: 441,171

[22] Filed: May 15, 1995

[51] Int. Cl.[6] ........................................ C07F 7/12
[52] U.S. Cl. ........................................ 556/469
[58] Field of Search ............................... 556/469

[56] References Cited

U.S. PATENT DOCUMENTS

| | | | |
|---|---|---|---|
| 2,380,995 | 7/1945 | Rochow | 260/607 |
| 3,704,260 | 11/1972 | Wynn | 260/448.2 E |
| 3,769,310 | 10/1973 | Viego | 260/448.2 P |
| 4,393,229 | 7/1983 | Ritzer et al. | 556/469 X |
| 4,500,724 | 2/1985 | Ward, III et al. | 556/472 |
| 4,552,973 | 11/1985 | Feldner et al. | 556/469 |
| 4,605,543 | 8/1986 | Lepage et al. | 556/469 X |
| 4,774,347 | 9/1988 | Marko et al. | 556/466 |

*Primary Examiner*—Paul F. Shaver
*Attorney, Agent, or Firm*—William F. Boley

[57] ABSTRACT

A redistribution process for enriching a low-boiling methylsilane mixture in a methylchlorosilane selected from a group consisting of dimethylhydrochlorosilane and trimethylchlorosilane. The process comprises contacting a low-boiling methylsilane mixture, resulting from the contact of methyl chloride with silicon, with alumina under non-equilibrium conditions at a temperature greater than about 150° C. The present inventors have discovered that the concentrations of dimethylhydrochlorosilane and trimethylchlorosilane reach maximum levels under non-equilibrium conditions occurring at a temperature greater than about 150° C. The process is also useful for facilitating the removal of olefin and chlorocarbon organic contaminants from the low-boiling methylsilane mixture.

14 Claims, No Drawings

METHOD FOR REDISTRIBUTION AND PURIFICATION OF METHYLSILANES

BACKGROUND OF INVENTION

The present invention is a redistribution process for enriching a low-boiling methylsilane mixture in a methylchlorosilane selected from a group consisting of dimethylhydrochlorosilane and trimethylchlorosilane. The process comprises contacting a low-boiling methylsilane mixture, resulting from the contact of methyl chloride with silicon, with alumina under non-equilibrium conditions at a temperature greater than about 150° C. The present inventors have discovered that the concentrations of dimethylhydrochlorosilane and trimethylchlorosilane reach maximum levels under non-equilibrium conditions occurring at temperatures greater than about 150° C. The present process is also useful for removing olefin and chlorocarbon organic contaminants from the low-boiling methylsilane mixture.

Methylchlorosilanes are the basic monomers from which a wide variety of organosilicon containing fluids, rubbers, and resins are formed. Commercially these methylchlorosilane monomers are produced by a process typically referred to as the "direct process." In the direct process, methyl chloride is reacted with silicon in the presence of a catalyst comprising copper. The process was first described by Rochow, U.S. Pat. No. 2,380,995. Commercially, production of polydimethylsiloxanes represent the highest volume use of methylchlorosilanes from the direct process. Therefore, considerable effort has been directed toward optimizing the direct process to produce dimethyldichlorosilane. Such optimization efforts are described in, for example, Ward et al., U.S. Pat. No. 4,500,724.

Despite all attempts to optimize the direct process for dimethyldichlorosilanes, the effluent from the reactor is still a mixture of methylsilanes and higher boiling materials which can include disilanes, polysiloxanes, silylmethylenes, and particulates. Typically the effluent exiting the reactor is distilled to separate the methylsilanes from the higher-boiling materials. The methylsilane distillate comprises a mixture having dimethyldichlorosilane as a major component and minor components comprising, for example, tetramethylsilane, dimethylhydrochlorosilane, methylhydrodichlorosilane, trimethylchlorosilane, and methyltrichlorosilane. These minor components can represent as much as 15 weight percent of the monosilanes produced in the direct process. Commercial demand for methylsilanes can at times make it desirable to increase the proportion of certain of these minor component methylsilanes, such as dimethylhydrochlorosilane and trimethylchlorosilane, in the direct process effluent. Although it is possible to alter the ratios of methylsilanes exiting the direct process reactor by changes to the process, manufacturers are reluctant to risk upsetting a process on which considerable resource has been expended to optimize for production of dimethyldichlorosilane. Therefore, methods are desirable to alter the product mix from the direct process exterior to the direct process reactor. The present method provides a process whereby the concentration of dimethylhydrochlorosilane and trimethylchlorosilane in the effluent from the direct process can be increased. The method comprises contacting a low-boiling methylsilane mixture, resulting from the reaction of methyl chloride with silicon, with alumina under non-equilibrium conditions at a temperature greater than about 150° C. Unexpectedly, the present inventors have found that under non-equilibrium conditions higher concentrations of dimethylhydrochlorosilane and trimethylchlorosilane can be obtained in the low-boiling methylsilane mixture than would be predicted by standard equilibrium calculations.

The present process is also useful for removing olefin and chlorocarbon organic contaminants from the low-boiling mixture. Under process conditions, olefin and chlorocarbon organic contaminants can be reacted with silicon-bonded hydrogen to convert the contaminants to saturated alkanes. Therefore, the present invention provides a process where redistribution of methylsilane and removal of olefin and chlorocarbon organic contaminants can be effected in a single step.

Wynn, U.S. Pat. No. 3,704,260, teaches that trimethylchlorosilane and methylhydrodichlorosilane can be rearranged in the presence of aluminum trichloride to form dimethylhydrochlorosilane. The rearrangement is preferably carried out at a temperature of about 110° C. to 140° C. for about 0.25 to 8 hours.

Viego et al., U.S. Pat. No. 3,769,310, teach the redistribution of methylhydrodichlorosilane with trimethylchlorosilane to produce dimethylhydrochlorosilane using a catalyst selected from a group consisting of $AlCl_3$, $KAlCl_4$, and $BF_3$. Viego et al. teach the process is to be run until equilibrium conditions are established at a temperature within a range of 50° C. to 250° C. and a time within a range of 2 to 7 hours.

Marko et al., U.S. Pat. No. 4,774,347, teach a process for reducing the chlorocarbon content of alkylsilanes. The process comprises contacting crude alkylsilanes containing as a minor portion chlorocarbons, and a hydrogen-containing silane with a catalyst that facilitates the reaction of the chlorocarbons with the hydrogen-containing silane to convert the chlorocarbons to an alkane. Marko et al. teach that alumina may be a useful catalyst in the process and that during conduct of the process some rearrangement of more highly alkylated silanes with other alkylhalosilanes may occur. Marko teaches the process can be run at a temperature within a range of about 25° C. to less than 150° C.

SUMMARY OF INVENTION

The present invention is a redistribution process for enriching a low-boiling methylsilane mixture in a methylchlorosilane selected from a group consisting of dimethylhydrochlorosilane and trimethylchlorosilane. The process comprises contacting a low-boiling methylsilane mixture, resulting from the contact of methyl chloride with silicon, with alumina under non-equilibrium conditions at a temperature greater than about 150° C. The present inventors have discovered that the concentrations of dimethylhydrochlorosilane and trimethylchlorosilane reach maximum levels under non-equilibrium conditions occurring at a temperature greater than about 150° C. The present process is also useful for facilitating the removal of olefin and chlorocarbon organic contaminants from the low-boiling methylsilane mixture.

DESCRIPTION OF INVENTION

The present invention is a process for enriching a low-boiling methylsilane mixture in a methylchlorosilane. The process comprises:
(A) contacting a low-boiling methylsilane mixture, resulting from the contact of methyl chloride with silicon metalloid, with alumina under non-equilibrium conditions at a temperature greater than about 150° C., and (B) recovering a methylsilane mixture enriched in a methylchlorosilane selected from a group consisting of dimethylhydrochlorosilane and trimethylchlorosilane.

The present process can be run in standard reactors for contacting liquids and gases with a heterogeneous catalyst. The process can be run as a continuous, semi-continuous, or batch process. Preferred is when the present process is run as a continuous process using a packed-bed of alumina as catalyst.

The low-boiling methylsilane mixture, resulting from the contact of methyl chloride with silicon, can comprise, for example, tetramethylsilane, trimethylchlorosilane, dimethyldichlorosilane, methyltrichlorosilane, dimethylhydrochlorosilane, and methylhydrodichlorosilane. The preferred low-boiling methylsilane mixture is a distilled effluent from a direct process for making methylsilanes by the contact of methyl chloride with silicon metalloid in the presence of a catalyst. Such a process is described, for example, in Ward et al., U.S. Pat. No. 4,500,724, which is incorporated by reference as a process from which a low-boiling methylsilane mixture can be isolated for use in the present process. Typical components in the effluent from a direct process for making methylsilanes are described for example in Wynn, U.S. Pat. No. 3,704,260 and Chadwick et al., U.S. Pat. No. 5,292,909. The effluent from a direct process for making methylsilanes can include monosilanes such as described above for the methylsilane mixture, higher-boiling components such as disilanes, siloxanes, and silylmethylenes, and solids such as silicon containing solids and insoluble compounds of copper and other metals. The effluent from the direct process may also contain olefins and chlorinated hydrocarbons.

By "low-boiling" it is meant that the methylsilane mixture comprises those compounds having a boiling point less than about 100° C. Preferred is when the low-boiling methylsilane mixture comprises those compounds having a boiling point less than about 70° C. More preferred is when the low-boiling methylsilane mixture is a low-boiling fraction resulting from the distillation of the product from a direct process reactor for making methylsilanes by the reaction of methyl chloride with silicon metalloid.

The low-boiling methylsilane mixture is contacted with alumina. In the present process the inventors believe that the alumina serves as a redistribution catalyst. It is preferred that the alumina have a low sodium content and have both high porosity and high surface area. More preferred is when the alumina has a porosity of at least about 0.4 cm$^3$/g and a surface area of at least 150 m$^2$/g. Even more preferred is when the alumina has a porosity of at least about 0.7 cm$^3$/g and a surface area of at least about 200 m$^2$/g. The upper limits for porosity and surface area are not limiting and are primarily determined by availability and the ability to contain and handle the material.

The concentration of alumina in relation to the low-boiling methylsilane mixture used in the present process is not critical and can be any concentration which effects enrichment of the low-boiling methylsilane mixture in the desired methylchlorosilane. In the preferred process, the process is run as a continuous process in a packed-bed reactor. In this case, the amount of alumina comprising the packed-bed will depend on such factors as acceptable pressure drop across the packed-bed and desired through put and residence time of the methylsilane mixture in the alumina bed.

The present process is run under non-equilibrium conditions. When the present process is run under non-equilibrium conditions, the low-boiling methylsilane mixture can be enriched in a methylchlorosilane selected from a group consisting of dimethylhydrochlorosilane and trimethylchlorosilane. By "enriched" it is meant that the amount of dimethylhydrochlorosilane and trimethylchlorosilane is increased over that amount present in the mixture prior to contact with the alumina and in addition is increased over that obtained in an equilibrium mixture. The present inventors have discovered that in the present process the maximum concentrations of dimethylhydrochlorosilane and trimethylchlorosilanes present in the low-boiling methylsilane mixture is achieved under nonequilibrium conditions. The non-equilibrium conditions at which this maximum is reached can easily be determined by those of ordinary skill in the art given the guidance provided herein, and such conditions depends upon the methylchlorosilane in which the low-boiling methylsilane mixture is to be enriched and the composition of the methylsilane mixture.

When it is desired to enrich the low-boiling methylsilane mixture in dimethylhydrochlorosilane, it is preferred that the low-boiling mixture comprise at least methylhydrodichlorosilane and trimethylchlorosilane and the nonequilibrium conditions comprise a temperature within a range of greater than about 150° C. to 300° C. and a contact time of the mixture with the alumina within a range of about 0.1 to 90 minutes. Preferred conditions for enriching the low-boiling methylsilane mixture in dimethylhydrochlorosilane is a temperature within a range of about 180° C. to 220° C. and a contact time of the mixture with the alumina within a range of about 5 to 60 minutes.

When it is desired to enrich the low-boiling methylsilane mixture in trimethylchlorosilane, it is preferred that the low-boiling mixture comprise at least tetramethylsilane and dimethyldichlorosilane and the non-equilibrium conditions comprise a temperature within a range of about 180° C. to 340° C. and a contact time of the mixture with the alumina within a range of about 30 to 120 minutes. Preferred conditions for enriching the low-boiling methylsilane mixture in trimethylchlorosilane is a temperature within a range of about 200° C. to 250° C. and a contact time of the mixture with the alumina within a range of about 45 minutes to 90 minutes.

The pressure at which the present process is run is not critical and can generally be within a range of about 0 psig to 200 psig. It is preferred that the present process be run with the low-boiling methylsilane mixture in the liquid phase. Therefore it is preferred that the present process be run at a pressure which, at the temperature the process is run, maintains a major portion of the low-boiling methylsilane mixture in the liquid phase. A preferred pressure is within a range of about 80 psig to 200 psig.

A methylsilane mixture enriched in a methylchlorosilane selected from a group consisting of dimethylhydrochlorosilane and trimethylchlorosilane is recovered from the present process. By "recovered" it is meant that the enriched methylsilane mixture is separated from the alumina. When the process is run as a continuous process in a fixed-bed reactor, recovery can consist merely of collecting the effluent from the reactor. Recovery of the enriched methylsilane mixture can further comprise such steps as filtration to remove residual alumina or other particulates and distillation to separate the enriched methylsilane mixture into individual methylsilane compounds or mixtures of methylsilanes compounds.

The present process is also useful for removing olefin and chlorocarbon organic contaminants from a low-boiling methylsilane mixture resulting from the contact of methyl chloride with silicon. Olefins are known to cause color problems in the preparation of methylsilanes and polyorganosiloxane intermediates and products. Chlorocarbons create a problem due to their thermal instability, potentially decomposing into an olefin and hydrogen chloride. These olefins and chlorocarbons can have boiling points similar enough to those of the methylsilanes as to make their separation from the methylsilanes by distillation difficult. In the present process the olefins and chlorocarbons can be reacted with silane species having hydrogen bonded to silicon in the presence of alumina to form alkanes. Marko et al., U.S. Pat. No. 4,774,347, describes a process where olefins and chlorocarbons can be reacted with silane species having hydrogen bonded to silicon in the presence of Lewis acid forming materials at a temperature less than 150° C. to form alkanes. The presence process extends the teachings of Marko et al., herein incorporated by reference, to include a process having a temperature greater than about 150° C.

The chlorocarbon materials which can be converted to alkanes can be, for example, 2-chloropropane, 1-chlorobutane, 2-chlorobutane, 2-chloro-2-methylpropane, 1-chloropentane, 2-chloro-2-methylbutane, 1-chlorohexane, 2-chlorohexane, 3-chloro-2-methylpentane, 2-chloro-2,3-dimethylbutane, 3-chlorooctane and 2-chlorodecane.

Olefins which can be converted to alkanes by the present process include the dehydrohalogenation by-products of the above listed chlorocarbons.

The silane having hydrogen bonded to silicon can be, for example, dichlorosilane, dimethylsilane, methylchlorosilane, methyldichlorosilane, dimethylchlorosilane, and trimethylsilane. The hydrogen-containing silane is normally a minor portion of the low-boiling methylsilane mixture. However, to assure that a sufficient quantity of the hydrogen bonded to silicon is present to maximize the conversion of olefins and chlorocarbons to saturated hydrocarbons, a silane having hydrogen bonded to silicon may be added to the low-boiling methylsilane mixture.

The following examples are provided to illustrate the present invention. These examples are not intended to limit the scope of the claims herein.

EXAMPLE 1

The redistribution of a low-boiling methylsilane mixture in a packed-bed of alumina was evaluated.

The reactor comprised a 1.9 cm inside diameter by 30 cm length stainless steel tube. The reactor was packed with 1.6 mm × 6.4 mm alumina pellets (United Catalysts, Louisville, Ky.). The reactor was immersed in a temperature controlled oil bath. A low-boiling methylsilane mixture comprising the methylsilanes reported in Table 1a was fed to the reactor at a rate providing a residence time within the reactor of 5 minutes. The pressure of the reactor was maintained at 100 psig. The "Control" values represent the concentration of the methylsilanes in the mixture prior to feed to the reactor. At the temperatures reported in Table 1 a sample of the effluent from the reactor was analyzed by gas chromatography using a thermal conductivity detector (GC-TC). The results of this analysis are reported in Table 1a. Also reported for comparison purposes is the calculated equilibrium concentrations for each of the methylchlorosilanes after redistribution ("Equil."). These calculations were made using standard thermodynamic calculations.

The effluent from the reactor was also analyzed by GC-TC for chlorocarbon content. Prior to passing through the reactor, the methylsilane mixture contained 792 ppm chlorocarbons. The percent reduction of chlorocarbons in the mixture at each reactor temperature is reported in Table 1b.

TABLE 1a

| Temp. (°C.) | Non-Equilibrium Redistribution of Methylsilane Mixture | | | | | |
|---|---|---|---|---|---|---|
| | Weight Percent | | | | | |
| | $Me_4Si$ | $Me_2HSiCl$ | $MeHSiCl_2$ | $Me_3SiCl$ | $MeSiCl_3$ | $Me_2SiCl_2$ |
| 90 | 0.08 | 1.25 | 4.14 | 2.75 | 6.05 | 84.73 |
| 120 | 0.01 | 1.19 | 4.14 | 2.88 | 6.08 | 84.78 |
| 150 | 0.00 | 1.13 | 3.80 | 2.91 | 6.19 | 85.10 |
| 180 | 0.00 | 1.51 | 3.43 | 3.02 | 6.79 | 84.32 |
| 210 | 0.00 | 1.72 | 3.12 | 3.15 | 7.38 | 83.61 |
| (Control) | 0.12 | 1.33 | 3.92 | 2.67 | 6.06 | 85.05 |
| (Equil.) | 0.00 | 1.15 | 3.89 | 3.68 | 6.92 | 83.51 |

TABLE 1b

| | Chlorocarbon Removal |
|---|---|
| Temp. (°C.) | % Reduction Chlorocarbons |
| 90 | 61 |
| 120 | 66 |
| 150 | 82 |
| 180 | 89 |
| 210 | 92 |

EXAMPLE 2

The redistribution of a second low-boiling methylsilane mixture in a packed-bed of alumina was evaluated at a residence time of five minutes. The reactor was as described in Example 1. A methylsilane mixture of the composition described in Table 2a as "Control" was fed to the reactor at a rate providing for a residence time in the reactor of 5 minutes. The pressure of the reactor was maintained at 100 psig. At the temperatures reported in Table 2a, a sample of the effluent from the reactor was collected and analyzed by GC-TC. The results of this analysis are reported in Table 2a. Also reported for comparison purposes is the calculated equilibrium concentrations for each of the methylsilanes after redistribution. The effluent from the reactor was also analyzed by GC-TC for olefin and chlorocarbon content. Prior to passing through the reactor, the methylsilane mixture contained 81 ppm olefins and 170 ppm chlorocarbons. The percent total reduction in olefins and chlorocarbons at each reactor temperature is reported in Table 2b.

TABLE 2a

Non-Equilibrium Redistribution of Methylsilane Mixture

| Temp. (°C.) | Weight Percent | | | | | |
| --- | --- | --- | --- | --- | --- | --- |
| | Me₄Si | Me₂HSiCl | MeHSiCl₂ | Me₃SiCl | MeSiCl₃ | Me₂SiCl₂ |
| 90 | 0.04 | 0.28 | 2.17 | 1.90 | 5.59 | 89.78 |
| 120 | 0.00 | 0.39 | 1.99 | 2.04 | 5.80 | 89.40 |
| 150 | 0.00 | 0.56 | 1.78 | 2.06 | 6.08 | 89.08 |
| 210 | 0.00 | 0.81 | 1.43 | 2.11 | 6.64 | 88.65 |
| 240 | 0.00 | 0.91 | 1.33 | 2.26 | 6.95 | 88.15 |
| (Control) | 0.07 | 0.31 | 2.25 | 1.87 | 5.59 | 89.62 |
| (Equil) | 0.00 | 0.55 | 2.00 | 3.56 | 7.60 | 86.08 |

TABLE 2b

Reduction in Olefins and Chlorocarbons

| Temp. (°C.) | % Reduction |
| --- | --- |
| 90 | 97 |
| 120 | 97 |
| 150 | 99 |
| 210 | 99 |
| 240 | 99 |

EXAMPLE 3

The methylsilane mixture of Example 2 was redistributed in a packed-bed of alumina at a residence time of minutes. The procedure was the same as described in Example 2 with the exception of the residence time. The results are reported in Table 3a. The effluent from the reactor was also analyzed by GC-TC for olefins and chlorocarbons content. The percent total reduction in olefins and chlorocarbons at each reactor temperature is reported in Table 3b.

TABLE 3a

Non-Equilibrium Redistribution of Methylsilane Mixture

| Temp. (°C.) | Weight Percent | | | | | |
| --- | --- | --- | --- | --- | --- | --- |
| | Me₄Si | Me₂HSiCl | MeHSiCl₂ | Me₃SiCl | MeSiCl₃ | Me₂SiCl₂ |
| 90 | 0.00 | 0.25 | 2.14 | 1.97 | 5.58 | 89.74 |
| 120 | 0.00 | 0.61 | 1.66 | 2.13 | 6.29 | 88.96 |
| 150 | 0.00 | 0.80 | 1.39 | 2.17 | 6.63 | 88.69 |
| 210 | 0.00 | 0.82 | 1.24 | 2.86 | 7.74 | 86.83 |
| 240 | 0.00 | 0.80 | 1.30 | 4.03 | 9.20 | 84.06 |
| (Control) | 0.07 | 0.31 | 2.25 | 1.87 | 5.59 | 89.62 |
| (Equil.) | 0.00 | 0.55 | 2.00 | 3.56 | 7.60 | 86.08 |

TABLE 3b

Reduction in Olefins and Chlorocarbons

| Temp. (°C.) | % Reduction |
| --- | --- |
| 90 | 99 |
| 120 | 99 |
| 150 | 100 |
| 210 | 98 |
| 240 | 98 |

We claim:

1. A process for enriching a low-boiling methylsilane mixture in a methylchlorosilane, the process comprising:

(A) contacting a low-boiling methylsilane mixture, resulting from the contact of methyl chloride with silicon metalloid, with alumina under non-equilibrium conditions at a temperature greater than about 150° C., and (B) recovering a methylsilane mixture enriched in a methylchlorosilane selected from a group consisting of dimethylhydrochlorosilane and trimethylchlorosilane.

2. A process according to claim 1, where the low-boiling methylsilane mixture comprises methylhydrodichlorosilane and trimethylchlorosilane and the non-equilibrium conditions comprise a temperature within a range of greater than about 150° C. to 300° C. and a contact time within a range of about 0.1 to 90 minutes and the methylsilane mixture is enriched in dimethylhydrochlorosilane.

3. A process according to claim 2, where the temperature is within a range of about 180° C. to 220° C. and the contact time is within a range of about 5 to 60 minutes.

4. A process according to claim 1, where the low-boiling methylsilane mixture comprises tetramethylsilane and dimethyldichlorosilane and the non-equilibrium conditions comprise a temperature within a range of about 180° C. to 340° C. and a contact time within a range of about 30 to 120 minutes and the methylsilane mixture is enriched in trimethylchlorosilane.

5. A process according to claim 4, where the temperature is within a range of about 200° C. to 250° C. and the contact time is within a range of about 45 to 90 minutes.

6. A process according to claim 1, where the process is conducted as a continuous process for contacting the low-boiling methylsilane mixture with a fixed-bed of the alumina.

7. A process according to claim 1, where the low-boiling methylsilane mixture has a boiling point less than about 100° C. and is a distillate of product from a process comprising the reaction of methyl chloride with silicon metalloid.

8. A process according to claim 1, where the low-boiling methylsilane mixture has a boiling point less than about 70° C. and is a distillate of product from a process comprising the reaction of methyl chloride with silicon metalloid.

9. A process according to claim 1, where the alumina has a porosity of at least about 0.4 cm$^3$/g and a surface area of at least 150 m$^2$/g.

10. A process according to claim 1, where the alumina has a porosity of at least about 0.7 cm$^3$/g and a surface area of at least about 200 m$^2$/g.

11. A process according to claim 1, where the low-boiling methylsilane mixture is contacted with the alumina at a pressure within a range of about 80 psig to 200 psig.

12. A process according to claim 1, where the low-boiling methylsilane mixture comprises a silane having hydrogen bonded to silicon and a contaminant selected from a group consisting of olefins and chlorocarbons and the recovered methylsilane mixture enriched in methylchlorosilane has a reduced concentration of the contaminant in comparison to that present in the low-boiling methylsilane mixture.

13. A process according to claim 2, where the low-boiling methylsilane mixture comprises a silane having hydrogen bonded to silicon and a contaminant selected from a group consisting of olefins and chlorocarbons and the recovered methylsilane mixture enriched in dimethylhydrochlorosilane has a reduced concentration of the contaminant in comparison to that present in the low-boiling methylsilane mixture.

14. A process according to claim 4, where the low-boiling methylsilane mixture comprises a silane having hydrogen bonded to silicon and a contaminant selected from a group consisting of olefins and chlorocarbons and the recovered methylsilane mixture enriched in trimethylsilane has a reduced concentration of the contaminant in comparison to that present in the low-boiling methylsilane mixture.

\* \* \* \* \*